United States Patent [19]

Böhshar et al.

[11] Patent Number: 5,298,541
[45] Date of Patent: Mar. 29, 1994

[54] ARYL PHOSPHONITES, A PROCESS FOR THEIR PRODUCTION AND THEIR USE FOR STABILIZING PLASTICS

[75] Inventors: Manfred Böhshar, Kelkheim; Hans-Jerg Kleiner, Kronberg; Gerhard Pfahler, Augsburg, all of Fed. Rep. of Germany

[73] Assignee: Hoechst Aktiengesellschaft, Frankfurt, Fed. Rep. of Germany

[21] Appl. No.: 776,387

[22] PCT Filed: May 16, 1990

[86] PCT No.: PCT/EP90/00787

§ 371 Date: Feb. 20, 1992

§ 102(e) Date: Feb. 20, 1992

[87] PCT Pub. No.: WO90/14349

PCT Pub. Date: Nov. 29, 1990

[30] Foreign Application Priority Data

May 20, 1989 [DE] Fed. Rep. of Germany ....... 3916502
Jul. 15, 1989 [DE] Fed. Rep. of Germany ....... 3923492

[51] Int. Cl.$^5$ .............. C08K 5/5393; C07F 9/6574; C07F 9/48
[52] U.S. Cl. .................. 524/126; 524/291; 524/135; 558/70; 558/83; 558/78; 558/134; 458/156; 458/190
[58] Field of Search ............... 558/70, 83, 190, 78, 558/134, 156; 524/126, 135

[56] References Cited

U.S. PATENT DOCUMENTS

| | | |
|---|---|---|
| 3,264,324 | 8/1966 | Gould et al. ............ 558/70 |
| 3,875,264 | 4/1975 | Hofer et al. ............ 558/156 |
| 3,903,208 | 9/1975 | Hofer et al. ............ 558/156 |
| 4,143,028 | 3/1979 | Spivack . |
| 4,238,422 | 12/1980 | Cozens et al. ............ 558/70 |
| 4,308,218 | 12/1981 | Hofer et al. ............ 558/70 |
| 4,406,842 | 9/1983 | Spivack . |
| 4,474,914 | 10/1984 | Spivack . |
| 4,481,317 | 11/1984 | Nakahara et al. . |
| 4,952,740 | 8/1990 | Juge et al. . |
| 4,999,393 | 3/1991 | Haruna ............ 558/83 |

FOREIGN PATENT DOCUMENTS

| | | |
|---|---|---|
| 2834871 | 3/1979 | Fed. Rep. of Germany . |
| 2562543 | 10/1985 | France . |
| 46-17896 | 5/1971 | Japan . |

OTHER PUBLICATIONS

Derwent Abs. of pub. Soviet appln. SU-897-797 (Polymer Prod. Res.), Apr. 7, 1980.
Derwent Abs. of pub. Japanese appln. JA 7117896 (Mitsubishi Rayon Co. Ltd.), May 19, 1971.
Hartman, W., et al., *J. Molecular Catalysis 48:* (Oct. 17, 1988).

*Primary Examiner*—Veronica P. Hoke
*Attorney, Agent, or Firm*—Connolly and Hutz

[57] ABSTRACT

A process for the preparation of aryl phosphonites of the formula V

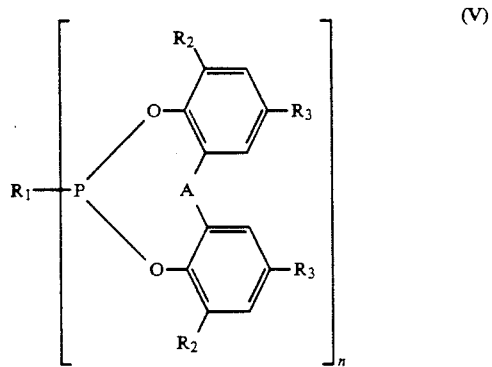

wherein the radicals and n are defined in the disclosure. The invention further relates to a plastic molding composition, in particular a polyolefin molding composition containing aryl phosphonites of the formula V.

17 Claims, No Drawings

ARYL PHOSPHONITES, A PROCESS FOR THEIR PRODUCTION AND THEIR USE FOR STABILIZING PLASTICS

DESCRIPTION

The present invention relates to new diaryl phosphonites and tetraaryl diphosphonites, a process for their preparation and their use for stabilizing plastics, in particular polyolefins.

It is known that synthetic polymers have to be protected against unwanted oxidative, thermal and photochemical damage during the preparation, the processing and the use by means of stabilizers or stabilizer systems. Such stabilizers comprise, for example, a phenolic antioxidant which should ensure in particular the long-term use stability of the molded article, and one or more costabilizers, which control the processing stability and in some cases also reinforce the synergistic effect of the phenolic component.

Conventional stabilizers include ortho-alkylated aryl phosphites and phosphonites, the latter being distinguished in particular by extensive stability to hydrolysis.

It is known from European Patent 5,447 (=U.S. Pat. Nos. 4,406,842 and 4,474,914=Japanese Laid-Open Application 79-141,753) that ortho-alkylated phenyl phosphonites of the formula

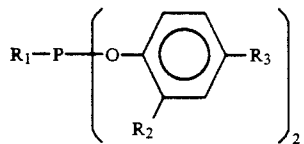

can be prepared by reaction of alkyl- or arylphosphonous dichlorides with ortho-alkylated phenols in the presence of at least stoichiometric amounts of a suitable base for neutralizing the hydrochloric acid formed. Although the general definitions given in this patent are specified to the extent that within preferred, relatively narrow definitions for the radicals $R_1$, $R_2$ and $R_3$, the radical $R_1$ can be phenyl, o-, m-, p-tolyl, o-, m-, p-xylyl, mesityl, o-cumyl, p-tert-butylphenyl, 2,4-di-tert-butylphenyl, 2,4,6-tri-tert-butylphenyl, or 2,4-di-tert-octylphenyl, $R_2$ can be tert-butyl, tert-amyl, tert-octyl, tert-octadecyl and $R_3$ can be H, methyl, i-propyl, tert-butyl, tert-amyl, n-hexyl, tert-octyl, tert-dodecyl or n-octadecyl, α-methylbenzyl or α,α-dimethylbenzyl; of the possible combinations among these, however, only two embodiment examples where $R_1$ is phenyl and $R_2$ and $R_3$ are simultaneously tert-butyl or tert-octyl are mentioned, and furthermore 6 table examples, in three of which $R_1$ is also phenyl and either $R_2$ is tert-octyl and $R_3$ is methyl or $R_2$ is tert-butyl and $R_3$ is hydrogen or $R_2$ and $R_3$ simultaneously are α,α-dimethylbenzyl. Accordingly, these 5 compounds cannot be deemed new.

However, the process of European Patent 5,447 can be carried out only to a limited extent because of the difficult synthesis of the dichlorophosphanes required as precursors, which is of course a disadvantage if an industrial preparation is taken into consideration. Thus, for example, of the aromatic derivatives, only phenyldichlorophosphane is an industrially available product, which makes derivatives of benzenephosphonous acid only available, which makes it easy to understand why, of the compounds in which $R_1$ is an aryl radical, precisely only those having unsubstituted phenyl are cited.

However, in order to meet the high demands made in practice on the stability, efficiency, nonvolatility and migration behavior of stabilizers for polymers, it is desirable that especially the more highly substituted derivatives of arylphosphonous acids be available. However, they are not accessible by known processes, due to the fact that until now the preparation of the precursors has not been economically feasible.

As a result, new stabilizers having improved properties and processes for their preparation, which do not have these disadvantages are very desirable.

Accordingly, the present invention relates to aryl phosphonites of the formula V (see formula sheet), i.e. diaryl phosphonites where $n=1$ and tetraaryl diphosphonites where $n=2$, in which A is non-existent—i.e. the two rings carry hydrogen—or a divalent hydrocarbon bridge having 1 to 6 carbon atoms which may be substituted by groups mentioned further below under $R^1$, or is a hetero atom such as oxygen or sulfur, cycloalkylidene having 4 to 8 carbon atoms or phenylalkylidene having 7 to 12 carbon atoms, $R^1$ as monovalent radical is a phenyl or benzyl radical, each of which carry 1 to 3 substituents, or is a-methylbenzyl, α,α-dimethylbenzyl, naphthyl or a naphthyl radical carrying 1 to 5 substituents, in which the substituents are identical or different and are a non-aromatic hydrocarbon radical, an alkoxy radical, an alkylthio radical or a dialkylamino radical, in which the alkyl radicals each have 1 to 8 carbon atoms, aryl or aryloxy each having 6 to 10 carbon atoms or halogen having an atomic number from 9 to 35, and as divalent radical a naphthylene radical which is unsubstituted or carries 1 to 4 non-aromatic hydrocarbon radicals each having 1 to 8 carbon atoms as substituents, or, if A is non-existent, a phenylene radical which is unsubstituted or is substituted by up to 2 non-aromatic hydrocarbon radicals each having 1 to 8 carbon atoms, $R^2$ is a non-aromatic hydrocarbon radical having 1 to 18 carbon atoms, aryl, arylmethyl, arylethyl or arylisopropyl, in which the aryl in each case contains 6 to 10 carbon atoms, and $R^3$ is hydrogen or a group mentioned under $R^2$, where, in the compounds in which $n=1$ and $R^1$ is phenyl, those are excepted in which simultaneously $R^2$ and $R^3$ are each tert-butyl, $R^2$ is tert-butyl and $R^3$ is hydrogen, $R^2$ is tert-octyl and $R^3$ is methyl, $R^2$ and $R^3$ are each tert-octyl and $R^2$ and $R^3$ are each α,α-dimethylbenzyl.

The specific class of compounds according to the invention in which A is non-existent has the formula I (see formula sheet) for the preparation of which diaryl halophosphonites II (see formula sheet) are used. In all cases, compounds in which $R^1$ is unsubstituted or substituted naphthyl are particularly preferred.

In the compounds of the formula I according to the invention, $R^1$ as monovalent radical is, for example, a phenyl or benzyl radical carrying 1 to 3 substituents, such as the $C_1$–$C_8$-alkyl, $C_1$–$C_8$-alkoxy, $C_1$–$C_8$-alkylthio radical, such as the alkyl radicals having 1 to 8 carbon atoms and mentioned individually under $R^2$ and the corresponding alkoxy and alkylthio radicals, or $C_5$–$C_8$-cycloalkyl, phenyl, phenoxy and/or halogen. Individual examples which may be mentioned are the tolyl, dimethylphenyl, triniethylphenyl, tert-butylphenyl, anisyl, naphthyl radicals which additionally can carry up to 2 alkyl carbon atoms, and the various biphenyl radicals, benzyl, α-methylbenzyl and α,α-dimethylbenzyl. Naturally the substituents in $R^1$ can only be combined in such a manner that no steric hindrance results. If $R^1$ contains 3 substituents, more than 5 carbon atoms together should not be contained in the two o-positions.

Examples of suitable $R^1$ as divalent radical are the various phenylene radicals, which are unsubstituted or carry 1 to 2 $C_1$-$C_8$, in particular $C_1$-$C_3$-alkyl groups, or the various naphthylene radicals, which are unsubstituted or substituted by 1 to 4 $C_1$-$C_8$-, in particular $C_1$-$C_3$-alkyl groups.

Examples of suitable radicals $R^2$ are non-aromatic hydrocarbon radicals having 1 to 18 carbon atoms, such as alkyl or cycloalkyl, furthermore aromatic radicals which, including aliphatic groups, have 6 to 18 carbon atoms, in which not more than 10 carbon atoms are part of an aromatic ring system. The radicals $R^2$ preferably contain 4 to 12 and in particular 6 to 10 carbon atoms. Individual examples of non-aromatic hydrocarbon radicals which may be mentioned are alkyl, such as methyl, ethyl, the various propyl, butyl, pentyl, hexyl, octyl, decyl, dodecyl, hexadecyl and octadecyl radicals, and cycloalkyl having 5 to 10 carbon atoms, such as cyclopentyl, cyclohexyl, cycloheptyl and cyclohexylmethyl (i.e. not only the hydrogenated benzyl radical but also the methylcyclohexyl radical); further examples are $C_8$-$C_{10}$-aryl, -arylmethyl, -arylethyl and -arylisopropyl, in which the term aryl in each case includes alkylaryl, carries not more 20, than three of the substituents mentioned under $R^1$ and including these has not more than 14 carbon atoms.

If the radical $R^2$ is an alkyl radical, tertiary alkyl radicals having 4–10 carbon atoms, such as tert-butyl, 2-methyl-2-butyl, 2-methyl-2-pentyl, 2-ethyl-2-butyl are particularly preferred. Other preferred compounds are those in which $R^2$ is phenyl, benzyl, α-methylbenzyl or α,α-dimethylbenzyl.

The invention also relates to a process for the preparation of aryl phosphonites of the formula V, in which A, additionally to the abovementioned meaning, can also be a direct bond, $R^1$ additionally to the abovementioned meaning can also be unsubstituted phenyl or benzyl as well as a nonaromatic hydrocarbon radical having 1 to 18 carbon atoms, such gas $C_1$-$C_{18}$-alkyl, and in compounds in which the two phenyl radicals are linked by A can also be biphenylene or substituted or unsubstituted phenylene, and $R^2$ and $R^3$ have the abovementioned meaning, which comprises first reacting in a first step a hydrocarbon halide $R^1(-Hal)_n$, in which $R^1$ has the previously mentioned meaning, n is=1 or 2 and the halogen has an atomic weight of at least 35, but is preferably chlorine or bromine, under Grignard conditions, that is, advantageously with intimate mixing, with at least molar amounts of magnesium to give the corresponding Grignard compounds $R^1(MgHal)_n$ and reacting these further in a second step with bisaryl halophosphonites of the formula VI (see formula sheet), in which $R^2$, $R^3$ and Hal have the abovementioned meaning, with the formation of bisaryl phosphonites V. The reaction can be accelerated and the degree of conversion improved if the magnesium is used in a small excess. Advantageously, 1.1 to 1.5 equivalents of magnesium are converted per halogen atom. Exposure to ultrasound during the Grignard reaction can in some cases be advantageous. This means that this process is also suitable for the preparation of the compounds where n=1 and which fall under the exceptional formulation of the product claim.

In the compounds of the formula VII Hal is preferably chlorine, in particular when compounds are prepared in which the two phenyl radicals are linked by A. This means that the process according to the invention is also suitable for the preparation of those compounds containing the group A which have been disclosed in European Patent 337,784, U.S. Pat. Nos. 4,143,028 and 4,481,317. The cyclic diaryl chlorophosphites of the formula VI used as starting compounds are available in a simple manner from corresponding bibphenols and phosphorus trichloride, for example by the process described in European Laid-Open Application 312,915.

The first step of the process according to the invention, which can be carried out in any conventional manner, is preferably carried out in an aprotic, organic solvent, such as an ether, for example diethyl, dipropyl or diisopropyl ether, ethylene glycol dimethyl or -diethyl ether, diethylene glycol dimethyl or -diethyl ether, methyl tert-butyl ether, dioxane or tetrahydrofuran.

Since the Grignard compounds are sensitive to hydrolysis and oxidation, it may be advantageous to work under an inert gas atmosphere. However, such a procedure is not absolutely necessary for the reaction to succeed. Particularly suitable inert gases are nitrogen and argon.

The reaction temperature is in general between 20° and 125° C., but preferably between 30° and 70° C.

To prepare the compounds I or V, the solution or suspension of the Grignard compound is metered in the second step to the diaryl halophosphonite II or VI, which advantageously is diluted with an inert, aprotic solvent, for example hexane, toluene, xylene or one of the above-mentioned ethers. The reactants in this step are combined slowly, in general between −30° C. and +30° C., but preferably between −20° C. and 20° C. As a rule, the reaction is exothermic; it can therefore be advantageous to control the course of the reaction by cooling. The most favorable results are obtained by using the reactants in stoichiometric amounts. However, it is also possible to use one reactant in excess; however, this is in general not associated with particular advantages. Advantageously, the mixture is stirred until the reaction is complete, which is promoted by heating to 0° to 30° C. and then the precipitated magnesium halide is separated off. The solvents can be removed from the filtrate in the usual manner, advantageously by distillation, in particular under reduced pressure.

The ester halides II or VI which are required as starting materials can be prepared in a simple manner from phosphorus trichloride and the corresponding phenols (for example U.S. Pat. No. 4,739,000). The purity of the starting materials thus obtained is about 85–90% (according to $^{31}$P-NMR).

The products V can be separated from the crude products by any desired method, but preferably by crystallization.

The synthesis of phosphonous esters by reaction of organometallic compounds with chlorophosphonous diesters has been described by various authors. They point out in particular that high-purity chlorophosphonous esters must be used as starting materials (Houben-Weyl, Methoden der Organischen Chemie (Methods of Organic Chemistry), volume 12/1, 329 (1963)). Nevertheless, the yields of diaryl phosphonites were only between about 33 and 75%. Since it is known that ester groups bound to the phosphorus atom basically display the same behavior towards organometallic compounds as halogen atoms (Houben-Weyl, Methoden der Organischen Chemie [Methods of Organic Chemistry], volume 12/1, 44 (1963)) it could not be expected—even if in contrast to customary practice no extremely pure chloroesters II or VII are used as starting materials—that the present process would provide the target compounds in such a satisfactory manner and largely without any yield-reducing competition reactions.

It is particularly surprising that the products are available by the process according to the invention in such a high yield and purity, since, according to the details of Japanese Laid-Open Application 57-46,993, phosphonous esters can in general only be obtained in economic yields by Grignard reactions if after the actual Grignard reaction various aftertreatment procedures with the addition of auxiliaries and under inert gas atmosphere are carried out.

As a result, the present invention has made it possible to obtain any desired substituted aryl phosphonites in a simple manner and with high yield and purity.

The invention finally relates to the use of the compounds of the formula V by themselves or in combination with a phenolic antioxidant for stabilizing plastics, such as polycarbonates, preferably plastics obtained by polymerization, such as polyolefins, in particular polypropylene. The compounds of the formula I provide the plastics in the molding compositions with improved stability to degradation by light, oxygen and heat. However, the purity of the resulting crude reaction product (85-93% according to $^{31}$P-NMR) is in most cases sufficient for this application. In this case, they do not have to be isolated in pure form.

Accordingly, the present invention also relates to a plastic molding composition comprising a thermoplastic or thermoset plastic and an aryl phosphonite of the formula V in a ratio of (90 to 99.99):(0.01 to 10), in which n is 1 or 2, A is non-existent—i.e. the two rings carry hydrogen—or a divalent hydrocarbon bridge having 1 to 6 carbon atoms which may be substituted by groups mentioned further below under $R^1$, or is a hetero atom such as oxygen or sulfur, cycloalkylidene having 4 to 8 carbon atoms or phenylalkylidene having 7 to 12 carbon atoms, $R^1$ as monovalent radical is a phenyl or benzyl radical, each of which carry 1 to 3 substituents, or is α-methylbenzyl, α,α-dimethylbenzyl, naphthyl or a naphthyl radical carrying 1 to 5 substituents, in which the substituents can be identical or different and are a non-aromatic hydrocarbon radical, an alkoxy radical, an alkylthio radical or a dialkylamino radical, in which the alkyl radicals each have 1 to 8 carbon atoms, aryl or aryloxy each having 6 to 10 carbon atoms or halogen having an atomic number from 9 to 35, and as divalent radical a naphthylene radical which is unsubstituted or carries 1 to 4 non-aromatic hydrocarbon radicals each having 1 to 8 carbon atoms as substituents, or, if A is non-existent, a phenyl radical which is unsubstituted or substituted by up to two non-aromatic hydrocarbon radicals having 1 to 8 carbon atoms, $R^2$ is a non-aromatic hydrocarbon radical of 1 to 18 carbon atoms, aryl, arylmethyl, arylethyl or arylisopropyl, in which the aryl in each case contains 6 to 10 carbon atoms, $R^3$ is hydrogen or a group mentioned under $R^2$, where, in the compounds in which n is 1 and $R^1$ is phenyl, those are excepted in which simultaneously $R^2$ and $R^3$ are each tert-butyl, $R^2$ is tert-butyl and $R^3$ is hydrogen, $R^2$ is tert-octyl and $R^3$ is methyl, $R^2$ and $R^3$ are each tert-octyl and $R^2$ and $R^3$ are each α,α-dimethylbenzyl.

Compounds of the formula I, in particular those containing no dialkylamino radicals, are preferred.

The plastic molding compound according to the invention contains a thermoplastic or thermoset organic polymer, for example one of the following:

1. Polymers of mono- and diolefins, for example polyethylene of high, medium or low density (which, if desired, can be crosslinked), polypropylene, polyisobutylene, poly-1-butene, polymethyl-1-pentene, polyisoprene or polybutadiene and polymers of cycloolefins, such as cyclopentene or norbornene.

2. Mixtures of the polymers mentioned under 1), for example of polypropylene with polyethylene or with polyisobutylene.

3. Copolymers of mono- and diolefins with one another or with other vinyl monomers, such as ethylene-propylene copolymers, propylene-1-butene copolymers, propyleneisobutylene copolymers, ethylene-1-butene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers and salts thereof (ionomers), and terpolymers of ethylene with propylene and a diene, such as hexadiene, dicyclopentadiene or ethylidenenorbornene.

4. Polystyrene.

5. Copolymers of styrene or α-methylstyrene with dienes or acrylic derivatives, such as styrene-butadiene, styrene-maleic anhydride, styrene-acrylonitrile, styrene-ethyl methacrylate, styrene-butadiene-ethyl acrylate, styrene-acrylonitrile-methyl acrylate; mixtures of high impact strength and composed of styrene copolymers and one other polymer, such as a polyacrylate, a diene polymer or an ethylene-propylene-diene terpolymer; and block copolymers of styrene, such as styrene-butadiene-styrene, styrene-isoprene-styrene, styrene-ethylene/butylene-styrene or styrene-ethylene/propylene-styrene.

6. Graft copolymers of styrene, such as styrene onto polybutadiene, styrene and acrylonitrile onto polybutadiene (ABS), styrene and maleic anhydride onto polybutadiene, styrene and alkyl acrylates or alkyl methacrylates onto polybutadiene, styrene and acrylonitrile onto ethylene-propylene-diene terpolymers, styrene and acrylonitrile onto poly(alkyl acrylates) or poly(alkyl methacrylates), styrene and acrylonitrile onto acrylatebutadiene copolymers, and mixtures thereof with the copolymers mentioned under 5), which are known, for example, as so-called ABS, MBS, ASA or AES polymers.

7. Halogen-containing polymers, such as polychloroprene, chlorinated rubber, chlorinated (CPE) or chlorosulfonated polyethylene, epichlorohydrin homo- and copolymers, in particular polymers of halogen-containing vinyl compounds, such as polyvinyl chloride (PVC), polyvinylidene chloride (PVDC), polyvinyl fluoride, polyvinylidene fluoride (PVDF); and the copolymers thereof, such as vinyl chloride-vinylidene chloride, vinyl chloride-vinyl acetate or vinylidene chloride-vinyl acetate.

8. Polymers derived from α,β-unsaturated carboxylic acids and derivatives thereof, such as polyacrylates and polymethacrylates, polyacrylamides and polyacrylonitriles.

9. Copolymers of the monomers mentioned under 8) with one another or with other unsaturated monomers, such as acrylonitrile-butadiene copolymers, acrylonitrile-alkyl acrylate copolymers, acrylonitrile-alkoxyacrylate copolymers, acrylonitrile-vinyl halide copolymers or acrylonitrile-alkyl methacrylate-butadiene terpolymers.

10. Polymers derived from unsaturated alcohols and amines or acyl derivatives or acetals thereof, such as polyvinyl alcohol, polyvinyl acetate, stearate, benzoate, maleate, polyvinylbutyral, polyallyl phthalate, polyallylmelamine.

11. Homo- and copolymers of cyclic ethers, such as polyethylene glycols, polyethylene oxide, polypropylene oxide or copolymers thereof with bisglycidyl ethers.

12. Polyacetals, such as polyoxymethylene (POM), and those polyoxymethylenes containing comonomers, such as ethylene oxide.

13. Polyphenylene oxides and sulfides.

14. Polyurethanes (PUR) derived on the one hand from polyethers, polyesters and polybutadienes having terminal hydroxyl groups and on the other hand from aliphatic or aromatic polyisocyanates and precursors thereof (polyisocyanates-polyels prepolymers).

15. Polyamides and copolyamides derived from dismines and dicarboxylic acids and/or from aminocarboxylic acids or the corresponding lactams, such as nylon-4, nylon-6, nylon-6/6, nylon-6/10, nylon-11, nylon-12, poly-2,4,4-trimethylhexamethyleneterephthalamide, poly-m-phenyleneisophthalamide, and copolymers thereof with polyethers, such as with polyethylene glycol, polypropylene glycol or polytetramethylene glycol.

16. Polyureas, polyamides and polyamidoimides.

17. Polyesters derived from dicarboxylic acids and diols and/or from hydroxycarboxylic acids or the corresponding lactones, such as polyethylene terephthalate, polybutylene terephthalate (PBTP), poly-1,4-dimethylolcyclohexane terephthalate, poly-(2,2-bis(4-hydroxyphenyl)propane) terephthalate, polyhydroxybenzoates, and block polyether esters derived from polyethylene having terminal hydroxyl groups, dialcohols and dicarboxylic acids.

18. Polycarbonates (PC).

19. Polysulfones and polyether sulfones.

20. Crosslinked polymers derived on the one hand from aldehydes and on the other hand from phenols, urea or melamine, such as phenol-formaldehyde, urea-formaldehyde and melamine-formaldehyde resins.

21. Drying and non-drying alkyd resins.

22. Unsaturated polyester resins derived from co-polyesters of saturated and unsaturated dicarboxylic acids with polyhydric alcohols, and vinyl compounds as cross-linking agents, as well as the halogen-containing, non-flammable modifications thereof.

23. Crosslinkable acrylic resins derived from substituted acrylic esters, such as from epoxy acrylates, urethane acrylates or polyester acrylates.

24. Alkyd resins, polyester resins and acrylate resins crosslinked with melamine resins, urea resins, polyisocyanates or epoxy resins.

25. Crosslinked epoxy resins derived from polyepoxides, for example from bis(glycidyl) ethers or from cycloaliphatic diepoxides.

26. Natural polymers, such as cellulose, natural rubber, gelatins and polymer-homologous chemically modified derivatives thereof, such as cellulose acetates, propionates and butyrates, and the cellulose ethers, such as methylcellulose.

27. Mixtures of the abovementioned polymers, such as, for example, PP/EPDM, nylon-6/EPDM or ABS, PVC/EVA, PVC/ABS, PVC/MBS, PC/ABS, PBTP/ABS, PC/ASA, PC/PBT, PVC/CPE, PVD/acrylate, POM/thermoplastic PUR, POM/acrylate, POM/MBS, polyphenylene ether/high impact strength polystyrene (PPE/HIPS) PPE/nylon-6.6 and copolymers, PA/HDPE, PA/PP, PA/PPE.

28. Naturally occurring and synthetic organic materials which are pure monomers or mixtures of monomers, such as mineral oils, animal and vegetable fats, oils and waxes, or oils, fats and waxes based on synthetic esters or mixtures of these materials.

29. Aqueous dispersions of natural or synthetic rubber.

The polymer is preferably a polyolefin, in particular polypropylene. The amount of the polymer in the molding compound according to the invention is 90 to 99.99, preferably 98 to 99.98% by weight.

The molding compound contains as stabilizer an aryl phosphonite of the formula I and, if necessary, a phenolic antioxidant.

The phenolic antioxidant is, for example, an ester of 3,3-bis(3'-t-butyl-4'-hydroxyphenyl)butyric acid of the formula III (see formula sheet), in which n is 1 or 2 and $R^4$ is a $C_1$–$C_{12}$-dlkyl radical, if n is 1, and a $C_1$–$C_{12}$-alkylene radical, if n is 2. Preferably, $R^4$ is a $C_2$–$C_4$-alkylene radical, in particular a $C_2$-alkylene radical.

However, the phenolic antioxidant can also be an ester of β-(3,5-di-t-butyl-4-hydroxyphenyl)propionic acid of the formula IV (see formula sheet), in which the alcohol component is a mono- to tetrahydric alcohol, such as methanol, octadecanol, 1,6-hexanediol, neopentyl glycol, diethylene glycol, triethylene glycol, pentaerythritol, tris(hydroxyethyl) isocyanurate, thiodiethylene glycol or dihydroxyethyloxamide.

The new stabilizers are incorporated in the organic polymers by generally customary methods. They can be incorporated, for example, by admixing the compounds and, if necessary, further additives to the melt before or during the molding. They can also be incorporated by applying the dissolved or dispersed compounds directly to the polymer or admixing to a solution, suspension or emulsion of the polymer, if appropriate subsequently allowing the solvent to evaporate. The amount to be added to the polymers is 0.01 to 10, preferably 0.025 to 5, in particular 0.05 to 1.0% by weight, relative to the material to be stabilized.

The new compounds can also be added in the form of a master batch containing these compounds, for example, in a concentration of 1 to 50, preferably 2.5 to 20% by weight, to the polymers which are to be stabilized.

In addition, the molding composition according to the invention can also contain other antioxidants, such as 1. alkylated monophenols, for example 2,6-di-t-butyl-4-methylphenol, -4-ethylphenol, -4-n-butylphenol, -4-i-butylphenol, 2-t-butyl-4,6-dimethylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol, 2,6-di-t-butyl-4-methoxymethylphenol;

2. alkylated hydroquinones, such as 2,5-di-t-butyl- and 2,5-di-t-amylhydroquinone, 2,6-di-t-butyl-4-methoxyphenol and 2,6-diphenyl-4-octadecyloxyphenol;

3. hydroxylated thiodiphenyl ethers, such as 2,2'-thio-bis(6-t-butyl-4-methylphenol) and -(4-octylphenol) and 4,4'-thio-bis(6-t-butyl-3-methylphenol) and -(6-t-butyl-2-methylphenol);

4. alkylidene bisphenols, such as 2,2'-methylene-bis(6-t-butyl-4-methylphenol), -(6-t-butyl-4-ethylphenol), -[4-methyl-6-(α-methylcyclohexyl)-phenol], -(4-methyl-6-cyclohexylphenol), -(6-nonyl-4-methylphenol), -(4,6-di-t-butylphenol), -[6-(α-methylbenzyl)-4-nonylphenol], -[6-(α,α-dimethylbenzyl)-4-nonylphenol], 4,4'-methylene-bis(2,6-di-t-butylphenol), -(6-t-butyl-2-methylphenol), 2,2'-ethylidene-bis(4,6-di-t-butylphenol) and -(6-t-butyl-4-isobutylphenol), 1,1-bis- and 1,1,3-tris(5-t-butyl-4-hydroxy-2-methylphenyl)butane, 2,6-di(3-t-butyl-5-methyl-2-hydroxybenzyl)-4-methylphenol, 1,1-bis(5-t-butyl-4-hydroxy-2-methylphenyl)-3-n-dodecylmercaptobutane, di(3-t-butyl-4-hydroxy-5-methylphenyl)dicyclopentadiene;

5. benzyl compounds, such as di[2-(3'-t-butyl-2-hydroxy-5'-methylbenzyl)-6-t-butyl-4-methylphenyl]terephthalate, 1,3,5-tri(3,5-di-t-butyl-4-hydroxybenzyl)-2,4,6-trimethylbenzene, di(3,5-di-t-butyl-4-hydroxybenzyl) sulfide, isooctyl 3,5-di-t-butyl-4-hydroxybenzylmercapto acetate, bis(4-t-butyl-3-hydroxy-2,6-dimethylbenzyl) dithiolterephthalate, 1,3,5-tris(3,5-di-t-butyl-4-hydroxybenzyl) isocyanurate, 1,3,5-tris(4-t-butyl-3-hydroxy-2,6-dimethylbenzyl) isocyanurate, dioctadecyl 3,5-di-t-butyl-4-hydroxybenzylphosphonate and the calcium salt of monoethyl 3,5-di-t-butyl-4-hydroxybenzylphosphonate;

6. acylaminophenols, such as 4-hydroxylaur- and -stearanilide, 2,4-bis(octylmercapto)-6-(3,5-di-t-butyl-4-hydroxyanilino)-s-triazine and octyl N-(3,5-di-t-butyl-4-hydroxyphenyl)carbamate;

7. esters of β-(5-t-butyl-4-hydroxy-3-methylphenyl) propionic acid with mono- or polyhydric alcohols, such as with methanol, octadecanol, 1,6-hexanediol, neopentyl glycol, diethylene glycol, triethylene glycol, pentaerythritol, tris(hydroxyethyl) isocyanurate, thiodiethylene glycol or dihydroxyethyloxamide;

8. amides of β-(3,5-di-t-butyl-4-hydroxyphenyl)propionic acid, such as N,N'-di(3,5-di-t-butyl-4-hydroxyphenylpropionyl)trimethylenediamine, -hexamethylenediamine and -hydrazine.

In addition, the molding composition according to the invention can contain further additives, such as 1. UV absorbers and light stabilizers, for example 1.1 2-(2'-hydroxymethyl)benzotriazoles, such as the 5'-methyl, 3',5'-di-t-butyl, 5'-t-butyl, 5'-(1,1,3,3-tetramethylbutyl), 5-chloro-3',5'-di-t-butyl, 5-chloro-3'-t-butyl-5'-methyl, 3'-sec.-butyl-5'-t-butyl, 4'-octoxy, 3',5'-di-t-amyl, 3',5'-bis(α,α-dimethylbenzyl) derivative;

1.2 2-hydroxybenzophenones, such as the 4-hydroxy, 4-methoxy, 4-octoxy, 4-decyloxy, 4-dodecyloxy, 4-benzyloxy, 4,2',4'-trihydroxy, 2'-hydroxy-4,4'-dimethoxy derivative;

1.3 esters of substituted or unsubstituted benzoic acids, such as phenyl salicylate, 4-t-butylphenyl salicylate, octylphenyl salicyalate [sic], dibenzoyl-resorcinol, bis(4-t-butylbenzoyl)resorcinol, benzoyl resorcinol, 2,4-di-t-butylphenyl 3,5-di-t-butyl-4-hydroxybenzoate, hexadecyl 3,5-di-t-butyl-4-hydroxybenzoate;

1.4 acrylates, such as ethyl or isooctyl α-cyano-β,β-diphenylacrylate, methyl α-carbomethoxy- and α-carbomethoxy-p-methoxycinnamate, methyl or butyl α-cyano-p-methyl-p-methoxycinnamate, N-(β-carbomethoxy-β-cyanovinyl)-2-methylindoline;

1.5 nickel compounds, such as nickel complexes of 2,2'-thiobis[4-(1,1,3,3-tetramethylbutyl)phenol], such as the 1:1 or 1:2 complex, if desired with additional ligands, such as n-butylamine, triethanolamine or N-cyclohexyldiethanolamine, nickel alkyl dithiocarbamates, nickel salts of monoalkyl 4-hydroxy-3,5-di-t-butylbenzylphosphonates, such as those of the methyl or ethyl ester, nickel complexes of ketoximes, such as those of 2-hydroxy-4-methylphenylundecylketonoxime, nickel complexes of 1-phenyl-4-lauroyl-5-hydroxypyrazole, if desired with additional ligands;

1.6 sterically hindered antines, such as 1.6.1 bis(2,2,6,6-tetramethylpiperidyl) sebacate, bis(2,2,6,6-tetramethylpiperidyl) glutarate and bis(2,2,6,6-tetramethylpiperidyl) succinate, bis(1,2,2,6,6-pentamethylpiperidyl) sebacate, bis(1,2,2,6,6-pentamethylpiperidyl) glutarate- and bis(1,2,2,6,6-pentamethylpiperidyl) succinate, 4-stearyloxy- and 4-stearoyloxy-2,2,6,6-tetramethylpiperidine, 4-stearyloxy- and 4-stearoyloxy-1,2,2,6,6-pentamethylpiperidine, 2,2,6,6-tetramethylpiperidyl behenate, 1,2,2,6,6-pentamethylpiperidyl behenate, 2,2,4,4-tetramethyl-7-oxa-3,20-diazadispiro-[5.1.11.2]heneicosan-2'-one, 2,2,3,4,4-pentamethyl-7-oxa-3,20-diazadispiro[5.1.11.2-]heneicosan-2'-one, 2,2,4,4-tetramethyl-3-acetyl-7-oxa-3,20-diazadispiro[5.1.11.2]heneicosan-2'-one, 2,2,4,4-tetramethyl-7-oxa-3,20-diaza-20-(β-lauryloxycarbonylethyl)-2'-oxo-dispiro-[5.1.11.2]heneicosane, 2,2,3,4,4-pentamethyl-7-oxa-3,20-diaza-20-(β-lauryloxycarbonylethyl)-2'-oxo-dispiro[5.1.11.2]heneicosane, 2,2,4,4-tetra-methyl-3-acetyl-7-oxa-3,20-diaza-20-(β-lauryloxycarbonylethyl)-2'-oxo-dispiro-[5.1.11.2]heneicosane, 1,1',3,3',5,5'-hexahydro-2,2',4,4',6,6'-hexaaza-2,2',6,6'-bismethano-7,8-dioxo-4,4'-bis(1,2,2,6,6-pentamethyl-4-piperidyl)biphenyl, N,N',N'',N'''-tetrakis{2,4-bis[N-(2,2,6,6-tetramethyl-4-piperidyl)butylamino]-1,3,5-triazin-6-yl}-4,7-diazadecane-1,10-diamine, N,N',N'',N'''-tetrakis{2,4-bis[N-(1,2,2,6,6-pentamethyl-4-piperidyl)-butylamino]-1,3,5-triazin-6-yl}-4,7-diazadecane-1,10-diamine, N,N',N'',N'''-tetrakis{2,4-bis[N-(2,2,6,6-tetramethyl-4-piperidyl)methoxy-propylamino]-1,3,5-triazin-6-yl}-4,7-diazadecane-1,10-diamine, N,N',N'',N'''-tetrakis{2,4-bis[N-(1,2,2,6,6-pentamethyl-4-piperidyl)methoxy-propylamino]-1,3,5-triazin-6-yl}-4,7-diazadecane-1,10-diamine, bis(1,2,2,6,6-pentamethylpiperidyl)-n-butyl-3,5-di-tert-butyl-4-hydroxybenzyl malonate, tris(2,2,6,6-tetramethyl-4-piperidyl) nitrilotriacetate, tetrakis(2,2,6,6-tetramethyl-4-piperidyl)-1,2,3,4-butanetetracarboxylic acid, 1,1'-(1,2-ethanediyl)bis(3,3,5,5-tetramethylpiperazinone);

1.6.2 poly-N,N'-bis(2,2,6,6-tetramethyl-4-piperidyl)-1,8-diazadecylene, condensation product of 1-(2-hydroxyethyl)-2,2,6,6-tetramethyl-4-hydroxypiperidine with succinic acid, condensation product of N,N'-bis(2,2,6,6-tetramethyl-4-piperidyl)-hexamethylenediamine with 4-tert-octylamino-2,6-dichloro-1,3,5-s-triazine, condensation product of N,N'-bis(2,2,6,6-tetramethyl-4-piperidyl)hexamethylenediamine with 4-morpholino-2,6-dichloro-1,3,5-triazine.

In many cases, a combination of the compounds according to the invention with the compounds mentioned under 1.6.1 proves especially advantageous.

1.7 oxamides, such as 4,4'-di-octyloxyoxanilide, 2,2'-di-octyloxy-5,5'-di-t-butyloxanilide, 2,2'-didodecyloxy-5,5'-di-t-butyloxanilide, 2-ethoxy-2'-ethyloxanilide, N,N'-bis(3-dimethylaminopropyl)oxamide, 2-ethoxy-5-t-butyl-2'-ethyloxanilide and its mixture with 2-ethoxy-2'-ethyl-5,4-di-t-butyloxanilide, mixtures of o- and p-methoxy- and -ethoxy-disubstituted oxanilides;

2. metal deactivators, such as N,N'-diphenyloxamide, N-salicylal-N'-salicyloylhydrazine, N,N'-bis-salicyloylhydrazine, N,N'-bis(3,5-di-t-butyl-4-hydroxyphenylpropionyl)hydrazine, 3-salicyloylamino-1,2,3-triazole, bis(benzylidene)oxalic dihydrazide;

3. phosphites and phosphonites, for example triphenyl phosphite, diphenylalkyl phosphites, phenyl dialkyl phosphites, tris(nonylphenyl) phosphite, trilauryl phosphite, trioctadecyl phosphite, distearyl pentaerythrityl diphosphite, tris(2,4-di-t-butylphenyl) phosphite, diisodecyl pentaerythrityl diphosphite, bis(2,4-di-t-butylphenyl) pentaerythrityl diphosphite, tristearyl sorbityl triphosphite, tetrakis-(2,4-di-t-butylphenyl)-4,4'-biphenylene diphosphonite, 3,9-bis(2,4-di-t-butylphenoxy)-2,4,8,10-tetraoxa-3,9-diphosphaspiro[5.5]undecane, tris(2-t-butyl-4-thio(2'-methenyl-4'-hydroxy-5'-t-butyl(phenyl-5-methenyl)phenyl phosphite.

4. peroxide-destroying compounds, such as esters of β-thiodipropionic acid, for example the lauryl, stearyl, myristyl or tridecyl ester, mercaptobenzimidazole, the zinc salt of 2-mercaptobenzimidazole, zinc alkyl dithiocarbamates, dioctadecyl sulfide, dioctadecyl monosulfide, pentaerythritol tetrakis-(β-dodecylmercapto)propionate;

5. basic co-stabilizers, such as melamine, polyvinylpyrrolidone, dicyandiamide, triallylcyanurate, urea derivatives, hydrazine derivatives, amines, polyamines, polyurethanes, alkali metal salts and alkaline earth metal salts of higher fatty acids or phenolates, for example calcium stearate, zinc stearate and magnesium stearate, sodium ricinoleate, potassium palmitate, antimony catecholate or tin catecholate, hydroxides and oxides of alkaline earth metals or of aluminum, for example CaO, MgO, ZnO;

6. nucleating agents, such as 4-t-butylbenzoic acid, adipic acid, diphenylacetic acid, dibenzylidenesorbitol;

7. fillers and reinforcing agents, such as calcium carbonate, silicates, glass fibers, asbestos, talc, kaolin, mica, barium sulfate, metal oxides and metal hydroxides, carbon black, graphite;

8. other additives, such as plasticizers, lubricants, emulsifiers, pigments, optical brighteners, flame retardants, antistats, blowing agents.

The various additional additives of the abovementioned groups 1 to 6 are added to the polymers to be stabilized in an amount of 0.01 to 10, preferably 0.01 to 5, % by weight, relative to the total weight of the molding composition. The relative amount of the additives from groups 7 and 8 is in general 1 to 80, preferably 10 to 50, % by weight, relative to the total molding composition.

The organic polymers stabilized according to the invention can be applied in various forms, for example as films, fibers, ribbons, profiles or as binders for paints, adhesives or putties.

In the examples 1 to 24 which follow, the compounds obtained according to the invention were crystallized using certain solvent mixtures. The ratios given are by volume. By changing the mixing ratios, it may be possible to achieve even better results.

Examples for the preparation of diaryl phosphonites

General Procedure for Compounds of the Formula I

Under a nitrogen atmosphere and with the exclusion of moisture, 250 mmol of organobromo compound and 250 mmol (=6.1 g) of Mg turnings in 170 ml of tetrahydrofuran were used to prepare the corresponding Grignard compound.

The solution or suspension obtained was then metered into the solution of 250 mmol of diaryl chlorophosphonite in 150 ml of n-hexane/tetrahydrofuran (2:1) at an internal temperature of $-20°$ to $-10°$ C. with vigorous stirring over a period of 30–40 min. The reaction mixture was then allowed to warm to room temperature, and stirring was continued for 2.5 hours to complete the reaction. After the precipitated Mg salt had been filtered off, the solvent was distilled off first in the vacuum of a water pump and then in a high vacuum, and the colorless or light beige residue obtained was powdered and dried in a high vacuum.

The amount of product in the crude materials was determined by $^{31}$P-NMR spectroscopy. It was in general between 85 and 93% (of the total product). To characterize the product, it was crystallized in the cases mentioned from acetonitrile/acetone mixtures.

1) Bis(2'4'-di-tert-butylphenyl) (2,4,6-trimethyl-1-phenyl)phosphonite: starting from 49.7 g of bromomesitylene and 119.3 g of bis(2,4-di-tert-butylphenyl) chlorophosphonite, 140 g of colorless material of a softening point of about 60° C. containing 90% of the above compound were obtained. Crystallization from acetonitrile/acetone (15:1) gave colorless crystals of melting point 95°–97° C.; [$^{31}$P-NMR: $\delta_{CDCl_3}$=168.4 ppm).

| $C_{37}H_{53}O_2P$ (560.8) | Calculated: Found: | 79.24% 78.9% | C, C, | 9.52% 9.7% | H, H, | 5.52% 5.3% | P P. |
|---|---|---|---|---|---|---|---|

2) Bis(2',4'-di-tert-butylphenyl) (2,4,5-trimethyl-1-phenyl)phosphonite: starting from 49.7 g of 5-bromo-1,2,4-trimethylbenzene and 119.3 g of bis(2,4-di-tert-butylphenyl) chlorophosphonite, 140 g of a yellowish material containing 93% of the above compound were obtained. Softening point about 30°–35° C.; [$^{31}$P-NMR: $\delta_{CDCl_3}$=155.4 ppm]. $C_{37}H_{53}O_2P$ (560.8).

3) Bis(2',4'-di-tert-butylphenyl) (4-tert-butylphenyl)phosphonite: starting from 53.3 g of p-bromo-tert-butylbenzene and 119.3 g of bis(2,4-di-tert-butylphenyl) chlorophosphonite, about 140 g of colorless material containing 90% of the above compound were obtained. Crystallization of the crude product from acetonitrile/acetone (15:2) gave colorless crystals of melting point 115°–117° C.; [$^{31}$P-NMR: $\delta_{CDCl_3}$=155.9 ppm].

| $C_{38}H_{55}O_2P$ | Calculated: | 79.4% | C, | 9.64% | H, | 5.38% | P |
| (574.82) | Found: | 79.8% | C, | 9.9% | H, | 5.0% | P. |

4) Bis(2'-tert-butylphenyl) (4-tert-butylphenyl)-phosphonite: starting from 53.3 g of p-bromo-tert-butylbenzene and 91.2 g of bis(2-tert-butylphenyl) chlorophosphonite, about 115 g of viscous resin containing 85% of the above compound were obtained. Crystallization of the crude product from acetonitrile/acetone (2:1) gave colorless crystals of melting point 95°–97° C.; [$^{31}$P-NMR: $\delta_{CDCl_3}$=155.9 ppm].

| $C_{30}H_{39}O_2P$ | Calculated: | 77.89% | C, | 8.49% | H, | 6.69% | P |
| (462.61) | Found: | 77.5% | C, | 8.7% | H, | 6.5% | P. |

5) Bis(2',4'-di-tert-butylphenyl) 1-naphthylphosphonite: starting from 51.8 g of 1-bromonaphthalene and 119.3 g of bis(2,4-di-tert-butylphenyl) chlorophosphonite, about 142 g of a colorless solid of softening point 50°–55° C. containing 91% of the above compound were obtained. Crystallization of the crude product from acetonitrile/acetone (5:1) gave colorless crystals of melting point 125°–127° C.; [$^{31}$P-NMR: $\delta_{CDCl_3}$=158.1 ppm].

| $C_{38}H_{49}O_2P$ | Calculated: | 80.24% | C, | 8.68% | H, | 5.44% | P |
| (568.77) | Found: | 80.5% | C, | 8.5% | H, | 5.3% | P. |

6) Bis(2',4'-di-tert-butylphenyl) (4-methyl-1-naphthyl)phosphonite: starting from 55.27 g of 1-bromo-4-methylnaphthalene and 119.3 g of bis(2,4-di-tert-butylphenyl) chlorophosphonite, about 140 g of a beige material containing 93% of the above compound were obtained. Crystallization from acetone gave colorless crystals of melting point 145°–146° C.; [$^{31}$P-NMR: $\delta_{CDCl_3}$=159.0 ppm].

| $C_{39}H_{51}O_2P$ | Calculated: | 80.37% | C, | 8.82% | H, | 5.31% | P |
| (582.80) | Found: | 80.7% | C, | 9.1% | H, | 5.1% | P. |

7) Bis(2'-tert-butylphenyl) (4-methyl-1-naphthyl)-phosphonite: starting from 55.27 g of 1-bromo-4-methylnaphthalene and 91.2 g of bis(2-tert-butylphenyl) chlorophosphonite, about 110 g of a yellow resin containing 90% of the above compound were obtained; [$^{31}$P-NMR: $\delta_{CDCl_3}$=158.4 ppm]. $C_{31}H_{35}O_2P$ (470.6).

8) Bis(2',4'-di-tert-butylphenyl) (2-methyl-1-naphthyl)phosphonite: starting from 55.27 g of 1-bromo-2-methylnaphthalene and 119.3 g of bis(2,4-di-tert-butylphenyl) chlorophosphonite, about 140 g of a yellowish material containing 90% of the above compound were obtained. Crystallization from acetone/acetonitrile (2:1) gave colorless crystals of melting point 157°–159° C.; [$^{31}$P-NMR: $\delta_{CDCl_3}$=164.4 ppm].

| $C_{39}H_{51}O_2P$ | Calculated: | 80.37% | C, | 8.82% | H, | 5.31% | P |
| (582.80) | Found: | 79.9% | C, | 9.1% | H, | 5.1% | P. |

9) Bis(2',4'-di-tert-butylphenyl) 2-naphthylphosphonite: starting from 51.8 g of 2-bromonaphthalene and 119.3 g of bis(2,4-di-tert-butylphenyl) chlorophosphonite, about 143 g of a colorless solid containing 94% of the above compound were obtained. Crystallization of the crude product from acetonitrile/acetone (9:1) gave colorless crystals of melting point 133°–135° C.; [$^{31}$P-NMR: $\delta_{CDCl_3}$=155.0 ppm].

| $C_{38}H_{49}O_2P$ | Calculated: | 80.24% | C, | 8.68% | H, | 5.44% | P |
| (568.77) | Found: | 80.4% | C, | 8.9% | H, | 5.2% | P. |

10) Bis(2',4'-di-tert-butylphenyl) (6-methoxy-2-naphthyl)phosphonite: starting from 59.3 g of 2-bromo-6-methoxynaphthalene and 119.3 g of bis(2,4-di-tert-butylphenyl) chlorophosphonite, 147 g of a colorless solid containing 93% of the above compound were obtained. Crystallization from acetone gave colorless crystals of melting point 146°–148° C.; [$^{31}$P-NMR: $\delta_{CDCl_3}$=155.9 ppm].

| $C_{39}H_{51}O_3P$ | Calculated: | 78.22% | C, | 8.58% | H, | 5.17% | P |
| (598.80) | Found: | 78.6% | C, | 8.3% | H, | 4.8% | P. |

11) Bis(2',4'-di-tert-butylphenyl) (4-methoxyphenyl)-phosphonite: starting from 46.75 g of 4-bromoanisole and 119.3 g of bis(2,4-di-tert-butylphenyl) chlorophosphonite, about 137 g of a colorless material of softening point 50° C. containing 93% of the above compound were obtained; [$^{31}$P-NMR: $\delta_{CDCl_3}$=155.8 ppm].

| $C_{35}H_{49}O_3P$ | Calculated: | 76.60% | C, | 9.00% | H, | 5.64% | P |
| (548.74) | Found: | 76.9% | C, | 9.2% | H, | 5.2% | P. |

12) Bis(2',4'-di-tert-butylphenyl) 4-biphenylphosphonite: starting from 58.3 g of 4-bromobiphenyl and 119.3 g of bis(2,4-di-tert-butylphenyl) chlorophosphonite, about 148 g of a colorless powder having a softening point of about 90° C. and containing 90% of the above compound were obtained [$^{31}$P-NMR : $\delta_{CDCl_3}$=154.8 ppm]. Crystallization from acetonitrile/acetone (10:1) gave colorless crystals of melting point 103°–105° C.

| $C_{40}H_{51}O_2P$ | Calculated: | 80.77% | C, | 8.64% | H, | 5.20% | P |
| (594.81) | Found: | 81.2% | C, | 8.8% | H, | 4.9% | P |

13) Bis(2',4'-di-tert-butylphenyl) 4-bromophenylphosphonite: starting from 59 g of 1,4-dibromobenzene and 119.3 g of bis (2,4-di-tert-butylphenyl) chlorophosphonite, about 145 g of an amorphous solid of softening point 80° C. containing about 85% of the above compound [$^{31}$P-NMR: $\delta_{CDCl_3}$=152.4 ppm] were obtained. $C_{34}H_{46}BrO_2P$ (597.61).

14) Tetra(2',4'-di-tert-butylphenyl) 1,4-phenylenediphosphonite: the abovementioned procedure was modified, and 500 mmol (=12.2 g) of magnesium and 500 mmol (=238 g) of bis(2,4-di-tert-butylphenyl) chlorophosphonite were used instead of 250 mmol per 250 mmol (=59 g) of 1,4-dibromobenzene to give about 200 g of the above compound of melting point 178°–180° C. from acetone [$^{31}$P-NMR: $\delta_{CDCl_3}$=153.1 ppm].

| $C_{62}H_{88}O_4P_2$ | Calculated: | 77.62% | C, | 9.24% | H, | 6.45% | P |
| (959.32) | Found: | 78.0% | C, | 9.0% | H, | 6.2% | P. |

15) Tetra(2',4'-di-tert-butylphenyl) 1,3-phenylenediphosphonite: Example 14 was repeated, except that 1,3-dibromobenzene was used, giving about 240 g of a beige solid containing about 70% of the above compound [$^{31}$P-NMR: $\delta_{CDCl_3}$=154.25 ppm] and a softening point of 70°–75° C.

General procedure for compounds of the formula V in which the two phenyl radicals are linked by A.

At first the procedure adopted was analogous to that in the preparation of compounds II, except that 250 mmol of the respective cyclic chlorophosphonite diester of the formula VI in 200 ml of tetrahydrofuran/n-hexane (2:1) were metered in at an internal temperature of −10° to 0° C. Stirring at 0° C. was then continued for 1 hour and at room temperature for 2.5 hours. After the precipitated magnesium halide had been filtered off and washed with 250 ml of tetrahydrofuran/n-hexane (4:1), the solvent was distilled off first in a vacuum of water pump and then in a high vacuum. The crude products were purified by crystallization.

16. 4,8-Di-tert-butyl-2,10-dimethyl-6-(1I-naphthyl)-12H-dibenzo[d,g][1,3,2]dioxaphosphocine: starting from 51.8 g of 1-bromonaphthalene and 101.2 g of 4,8-di-tert-butyl-6-chloro-2,10-dimethyl-12H-dibenzo[d,g][1,3,2]dioxaphosphocine, 94.3 g (=76%) of the above compound were obtained from acetone in the form of colorless crystals of melting point 251°–253° C.

| $C_{33}H_{37}O_2P$ | Calculated: | 79.81% C, | 7.50% H, | 6.23% P |
|---|---|---|---|---|
| (496.62) | Found: | 79.4% C, | 7.8% H, | 6.0% P. |

17. 4,8-Di-tert-butyl-2,10-diethyl-6-(1I-naphthyl)-12H-dibenzo[d,g][1,3,2]dioxaphosphocine: starting from 51.8 g of 1-bromonaphthalene and 108.2 g of 4,8-di-tert-butyl-6-chloro-2,10-diethyl-12H-dibenzo(d,g)[1,3,2]dioxaphosphocine, 106.2 g (=81%) of the above compound were obtained from acetonitrile in the form of colorless crystals of melting point 206°–208° C.

| $C_{35}H_{41}O_2P$ | Calculated: | 80.12% C, | 7.87% H, | 5.90% P |
|---|---|---|---|---|
| (524.68) | Found: | 79.5% C, | 7.8% H, | 5.7% P. |

18. 4,8-Di-tert-butyl-2,10-diethyl-6-(2′-naphthyl)-12H-dibenzo[[d,g][1,3,2]dioxaphosphocine: starting from 51.8 g of 2-bromonaphthalene and 108.2 g of 4,8-di-tert-butyl-6-chloro-2,10-diethyl-12H-dibenzo[d,g][1,3,2]dioxaphosphocine, 109 g (=83%) of the above compound were obtained from acetonitrile in the form of colorless crystals of melting point 222°–224° C.

| $C_{35}H_{41}O_2P$ | Calculated: | 80.12% C, | 7.87% H, | 5.90% P |
|---|---|---|---|---|
| (524.68) | Found: | 79.9% C, | 8.1% H, | 5.7% P. |

19. 4,8-Di-tert-butyl-2,10-dimethyl-6-(4′-methyl-1′-naphthyl)-12H-dibenzo[d,g][1,3,2]dioxaphosphocine: starting from 55.27 g of 1-bromo-4-methylnaphthalene and 101.2 g of 4,8-di-tert-butyl-6-chloro-2,10-dimethyl-12H-dibenzo[[d,g][1,3,2]dioxaphosphocine, 95.7 g (=75%) of the above compound were obtained from acetone/dichloromethane (5:1) in the form of colorless crystals of melting point 273°–276° C.

| $C_{34}H_{39}O_2P$ | Calculated: | 79.97% C, | 7.70% H, | 6.06% P |
|---|---|---|---|---|
| (510.66) | Found: | 79.3% C, | 7.8% H, | 6.1% P. |

20. 4,8-Di-tert-butyl-2,10-diethy-6-(4′-methyl-1′-naphthyl)-12H-dibenzo[d,g][1,3,2]dioxaphosphocine: starting from 55.27 g of 1-bromo-4-methylnaphthalene and 108.2 g of 4,8-di-tert-butyl-6-chloro-2,10-diethyl-12H-dibenzo[d,g][1,3,2]dioxaphosphocine, 100 g (=74%) of the above compound were obtained from acetone in the form of colorless crystals of melting point 258°–260° C.

| $C_{36}H_{43}O_2P$ | Calculated: | 80.26% C, | 8.04% H, | 5.74% P |
|---|---|---|---|---|
| (538.71) | Found: | 79.9% C, | 8.3% H, | 5.4% P. |

21. 4,8-Di-tert-butyl-2,10-diethyl-6-(4′-biphenyl)-12H-dibenzo[d,g][1,3,2]dioxaphosphocine: starting from 58.3 g of 4-bromobiphenyl and 108.2 g of 4,8-di-tert-butyl-6-chloro-2,10-diethyl-12H-dibenzo[d,g][1,3,2]dioxaphosphocine, 103.3 g (=75%) of the above compound were obtained from acetonitrile in the form of colorless crystals of melting point 170°–172° C.

| $C_{37}H_{43}O_2P$ | Calculated: | 80.70% C, | 7.87% H, | 5.62% P |
|---|---|---|---|---|
| (550.72) | Found: | 80.2% C, | 7.9% H, | 5.4% P. |

22. 4,8-Di-tert-butyl-2,10-diethyl-6-(2′,4′,5′-trimethyl-1′-phenyl)-12H-dibenzo[d,g][1,3,2]dioxaphosphocine: starting from 49.7 g of 5-bromo-1,2,4-trimethylbenzene and 108.2 g of 4,8-di-tert-butyl-6-chloro-2,10-diethyl-12H-dibenzo[d,g)[1,3,2]dioxaphosphocine, 113.7 g (=88%) of the above compound were obtained from acetonitrile/acetone (1:1) in the form of colorless crystals of melting point 198°–200° C.

| $C_{34}H_{45}O_2P$ | Calculated: | 79.03% C, | 8.77% H, | 6.0% P |
|---|---|---|---|---|
| (516.70) | Found: | 79.3% C, | 8.7% H, | 5.8% P. |

23. 4,4′-Biphenylene-bis[4,8-di-tert-butyl-2,10-diethyl-6-yl-12H-dibenzo[d,g][1,3,2]dioxaphosphocine]: the general procedure was modified, and 200 mmol (=62.4 g) of 4,4′-dibromobiphenyl were subjected to a Grignard reaction with 600 mmol (=14.6 g) of magnesium turnings in 300 ml of tetrahydrofuran with exposure to ultrasound (40 kHz) and then reacted with 400 mmol (=173.2 g) of 4,8-di-tert-butyl-6-chloro-2,10-diethyl-12H-dibenzo[d,g][1,3,2]dioxaphosphocine in 250 ml of tetrahydrofuran. After evaporation of the solvent, about 190 g of a solid remained containing (by $^{31}$P-NMR) 73% of the above compound ($^{31}$P-NMR: $\sigma_{CDCl_3}$=163.7 ppm). Colorless crystals of melting point 320° C. (decomposition) were obtained from acetone.

| $C_{62}H_{75}O_4P_2$ | Calculated: | 78.61% C, | 8.08% H, | 6.54% P |
|---|---|---|---|---|
| (947.23) | Found: | 78.3% C, | 8.2% H, | 6.3% P. |

24. 4,4′-Biphenylene-bis[4,8-di-tert-butyl-2,10-dimethyl-6-yl-12H-dibenzo[d,g][1,3,2]dioxaphosphocine]: the procedure was analogous to that of the previous example, except that the Grignard reagent was reacted with 400 mmol (=162 g) of 4,8-di-tert-butyl-6-chloro-2,10-dimethyl-12H-dibenzo[d,g][1,3,2]dioxaphosphocine. About 180 g of a solid remained, containing (by $^{31}$P-NMR) 72% of the above compound ($^{31}$P-NMR: $\sigma_{CDCl_3}$=163.9 ppm). Colorless crystals of melting point 306°–310° C. (decomposition) were obtained from acetone.

| $C_{58}H_{68}O_4P_2$ | Calculated: | 78.17% C, | 7.69% H, | 6.97% P |
| (891.12) | Found: | 77.8% C, | 7.8% H, | 6.7% P. |

II. WORKING EXAMPLES

The phosphonites according to the invention listed below were used for the experiments.

25 and 31: Bis(2',4'-di-tert-butylphenyl) 4-biphenylphosphonite according to Example 12, contained about 98% by $^{31}$P-NMR 26 and 32: Bis(2',4'-di-tert-butylphenyl) β-naphthylphosphonite according to Example 9, contained about 98% by $^{31}$P-NMR 27 and 33: Tetra(2',4'-di-tert-butylphenyl) 1,4-phenylenediphosphonite according to Example 14, contained about 95% by $^{31}$P-NMR 28 and 34: Bis(2',4'-di-tert-butylphenyl) (4-methyl-1-naphthyl)phosphonite according to Example 6

29 and 35: Bis(2,4-di-tert-butylphenyl) 2-methylnaphthylphosphonite according to Example 8

30 and 36: Bis(2,4-di-tert-butylphenyl) (2-methoxy-6-naphthyl)phosphonite according to Example 10

25 TO 30 AND COMPARATIVE EXAMPLES A TO C 100.0 g of unstabilized polypropylene powder (density: 0.903 g/cm$^3$; melt flow index MFI 230/5: 4 g/10 min) were mixed with 0.1 g of Ca stearate as acid acceptor and the amounts of phosphorus compound listed in the tables and extruded several times by means of a laboratory extruder (short-compression zone screw, diameter of screw 20 mm; length 400 mm, length of nozzle 30 mm, diameter [lacuna] mm; speed: 125 rpm; temperature program: 200°/230°/230° C.). After the 1st, 5th and 10th pass, samples were removed from the granules and used to measure the melt flow index according to DIN 53 735 and the yellowness as yellowness index according to ASTM D 1925-70. In addition, the granules of the 1st pass were used to produce extruded sheets of the dimensions 60×60×1 mm, and the yellowness was measured immediately and after hot storage (7 days at 100° C.).

The results are listed in Tables 1, 2 and 5.

31 TO 36 AND COMPARATIVE EXAMPLES D TO F 100.0 g of unstabilized polypropylene powder (density: 0.903 g/cm$^3$; melt flow index MFI 230/5: 4 g/10 min) were mixed with 0.1 g of Ca stearate as acid acceptor and 0.05 g of ethylene glycol bis(3,3-bis(3'-t-butyl-4'-hydroxyphenyl)butyrate and the amounts of phosphorus compound listed in the tables and extruded several times by means of a laboratory extruder (short-compression zone screw, diameter of screw 20 mm; length 400 mm, length of nozzle 30 mm, 2 mm diameter; speed: 125 rpm; temperature program: 200°/230°/230° C.). After the 1st, 5th and 10th pass, samples were removed from the granules and used to measure the melt flow index according to DIN 53 735 and the yellowness as yellowness index according to ASTM D 1925-70. In addition, the granules of the 1st pass were used to produce extruded sheets of the dimensions 60×60×1 mm, and the yellowness was measured immediately and after hot storage (7 days at 100° C.).

The results are listed in Tables 3, 4 and 5.

TABLE 1

The effect of phosphorus compounds on the processing stability of polypropylene. Melt flow index MFI 230/5 after multiple granulation. (MFI in g/10 min)

| | | MFI after | | |
|---|---|---|---|---|
| Example | Phosphorus compound | 1st | 5th | 10th granulation |
| Comp. A | none | 10 | 15.3 | 22.2 |
| Comp. B | 0.1 g of tris(2,4-di-t-butylphenyl) phosphite | 6.4 | 7.0 | 10.5 |
| Comp. C | 0.1 g of commercial phosphite*) | 5.5 | 5.7 | 7.8 |
| 25 | 0.1 g of (phosphonite according to the invention) | 6.15 | 7.8 | 11.0 |
| 26 | 0.1 g of (phosphonite according to the invention) | 6.4 | 6.7 | 7.16 |
| 27 | 0.1 g of (phosphonite according to the invention) | 6.2 | 7.3 | 8.6 |
| 28 | 0.1 g of (phosphonite according to the invention) | 6.1 | 6.3 | 11.3 |
| 29 | 0.1 g of (phosphonite according to the invention) | 6.6 | 8.0 | 9.4 |
| 30 | 0.1 g of (phosphonite according to the invention) | 5.4 | 6.0 | 5.9 |

*)Tetrakis(2,4-di-t-butylphenyl) 4,4'-biphenylenediphosphonite

TABLE 2

Change in color (yellowness index according to ASTM D 1925-70) after multiple granulation of polypropylene.

| | | MFI [sic] after | | |
|---|---|---|---|---|
| Example | Phosphorus compound | 1st | 5th | 10th granulation |
| Comp. A | none | 18.7 | 25.7 | 27.7 |
| Comp. B | 0.1 g of tris(2,4-di-t-butylphenyl) phosphite | 13.3 | 23.0 | 30.4 |
| Comp. C | 0.1 g of commercial phosphite*) | 12.8 | 21.0 | 26.1 |
| 25 | 0.1 g of (phosphonite according to the invention) | 21.5 | 34.4 | 39.5 |
| 26 | 0.1 g of (phosphonite according to the invention) | 8.0 | 16.4 | 27.0 |
| 27 | 0.1 g of (phosphonite according to the invention) | 15.8 | 27.7 | 36.7 |
| 28 | 0.1 g of (phosphonite according to the invention) | 9.8 | 18.3 | 27.3 |
| 29 | 0.1 g of (phosphonite according to the invention) | 20.6 | 24.0 | 32.0 |
| 30 | 0.1 g of (phosphonite according to the invention) | 7.4 | 11.7 | 16.3 |

*)Tetrakis(2,4-di-t-butylphenyl) 4,4'-biphenylenediphosphonite

TABLE 3

The effect of phosphorus compounds on the processing stability of polypropylene. Melt flow index MFI 230/5 after multiple granulation. (MFI in g/10 min)

| | | MFI after | | |
|---|---|---|---|---|
| Example | Phosphorus compound | 1st | 5th | 10th granulation |
| Comp. D | none | 6.3 | 8.8 | 14.9 |
| Comp. E | 0.05 g of tris(2,4-di-t-butylphenyl) phosphite | 5.2 | 6.4 | 6.4 |
| Comp. F | 0.05 g of commercial phosphite*) | 4.9 | 5.5 | 6.4 |
| 31 | 0.05 g of (phosphonite according to the invention) | 4.1 | 5.7 | 6.7 |
| 32 | 0.05 g of (phosphonite according to the invention) | 4.3 | 4.3 | 4.4 |
| 33 | 0.05 g of (phosphonite according to the invention) | 4.3 | 4.8 | 5.2 |
| 34 | 0.05 g of (phosphonite according to the invention) | 4.4 | 4.4 | 5.4 |
| 35 | 0.05 g of (phosphonite according to the invention) | 4.4 | 5.8 | 7.1 |
| 36 | 0.05 g of (phosphonite according | 4.6 | 4.9 | 5.6 |

TABLE 3-continued

The effect of phosphorus compounds on the processing stability of polypropylene. Melt flow index MFI 230/5 after multiple granulation. (MFI in g/10 min)

| Example | Phosphorus compound | 1st | 5th | MFI after 10th granulation |
|---|---|---|---|---|
| | to the invention) | | | |

*)Tetrakis(2,4-di-t-butylphenyl) 4,4'-biphenylenediphosphonite

TABLE 4

Change of color (yellowness index according to ASTM D 1925-70) after multiple granulation of polypropylene.

| Example | Phosphorus compound | 1st | 5th | YI after 10th granulation |
|---|---|---|---|---|
| Comp. D | none | 13.7 | 32.7 | 35.5 |
| Comp. E | 0.05 g of tris(2,4-di-t-butylphenyl) phosphite | 15.5 | 27.8 | 36.1 |
| Comp. F | 0.05 g of commercial phosphite*) | 8.7 | 19.4 | 26.0 |
| 31 | 0.05 g of (phosphonite according to the invention) | 8.7 | 23.2 | 33.4 |
| 32 | 0.05 g of (phosphonite according to the invention) | 9.2 | 14.9 | 19.3 |
| 33 | 0.05 g of (phosphonite according to the invention) | 10.0 | 15.1 | 21.0 |
| 34 | 0.05 g of (phosphonite according to the invention) | 10.3 | 16.8 | 22.4 |
| 35 | 0.05 g of (phosphonite according to the invention) | 14.7 | 30.2 | 38.5 |
| 36 | 0.05 g of (phosphonite according to the invention) | 12.5 | 23.0 | 30.0 |

*)Tetrakis(2,4-di-t-butylphenyl) 4,4'-biphenylenediphosphonite

TABLE 5

Change in color on 1 mm extruded sheets immediately after production and after heat treatment (7 days at 100° C.)

| | YI immediately | YI after 7 days |
|---|---|---|
| Comp. A | 4.2 | 10.1 |
| Comp. B | 3.4 | 13.0 |
| Comp. C | 4.5 | 12.5 |
| 25 | 6.2 | 14.9 |
| 26 | 2.7 | 9.9 |
| 27 | 3.8 | 13.1 |
| 28 | 2.7 | 10.8 |
| 29 | 3.3 | 13.3 |
| 30 | 2.2 | 10.6 |
| Comp. D | 3.5 | 5.6 |
| Comp. E | 4.7 | 6.6 |
| Comp. F | 2.9 | 3.8 |
| 31 | 2.2 | 3.2 |
| 32 | 2.4 | 3.4 |
| 33 | 2.5 | 3.5 |
| 34 | 2.6 | 4.0 |
| 35 | 4.1 | 6.0 |
| 36 | 3.5 | 4.6 |

Formula sheet

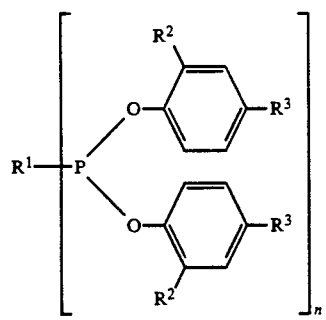

(I)

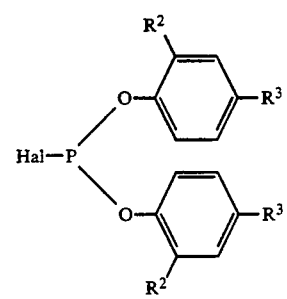

(II)

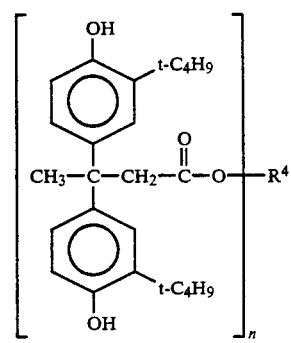

(III)

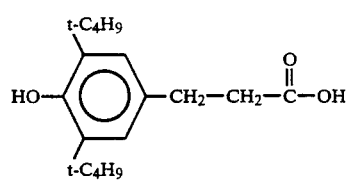

(IV)

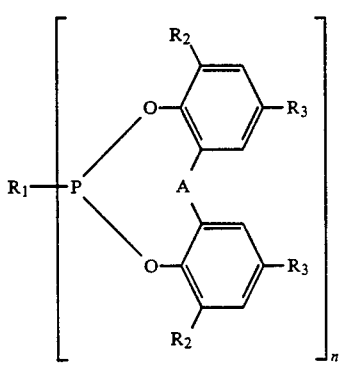

(V)

-continued
Formula sheet

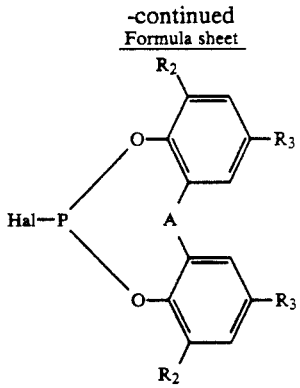

We claim:
1. A process for the preparation of aryl phosphonites of the formula (V)

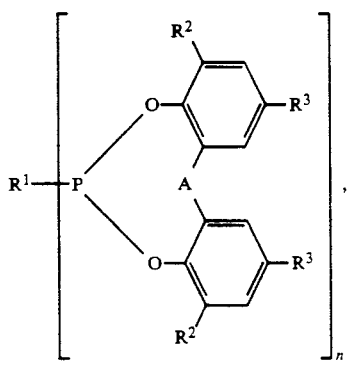

in which A is non-existent or a direct bond or a divalent hydrocarbon bridge having 1 to 6 carbon atoms which may be substituted by groups mentioned further below under $R^1$, or is a hetero atom, cycloalkylidene having 4 to 8 carbon atoms or phenylalkylidene having 7 to 12 carbon atoms, n is 1 or 2, $R^1$ as monovalent radical is a non-aromatic hydrocarbon radical having 1 to 18 carbon atoms, a phenyl or benzyl radical, each of which can carry 1 to 3 substituents, or is α-methylbenzyl, α,α-dimethylbenzyl, naphthyl or a naphthyl radical carrying 1 to 5 substituents, in which the substituents are identical or different and are a non-aromatic hydrocarbon radical, an alkoxy radical, an alkylthio radical or a dialkylamino radical, in which the alkyl radicals each have 1 to 8 carbon atoms, aryl or aryloxy each having 6 to 10 carbon atoms or halogen having an atomic number from 9 to 35, and as divalent radical a phenylene radical which is unsubstituted or is substituted by up to 2 non-aromatic hydrocarbon radicals each having 1 to 8 carbon atoms or a naphthylene radical which is unsubstituted or carries 1 to 4 non-aromatic hydrocarbon radicals each having 1 to 8 carbon atoms as substituents; or, if both phenyl radicals are bonded via A, can also be biphenylene, $R^2$ is a non-aromatic hydrocarbon radical having 1 to 18 carbon atoms, aryl, arylmethyl, arylethyl or arylisopropyl, in which the aryl in each case contains 6 to 10 carbon atoms, and $R^3$ is hydrogen or a group mentioned under $R^2$, which comprises reacting in a first step a hydrocarbon halide $R^1(-Hal)_n$, in which $R^1$ has the above-mentioned meaning, n is=1 or 2 and the halogen has an atomic weight of at least 35, under Grignard conditions with at least molar amounts of magnesium to give the corresponding Grignard compounds $R^1(MgHal)_n$ and reacting these in a second step with bisaryl halophosphonites of the formula VI

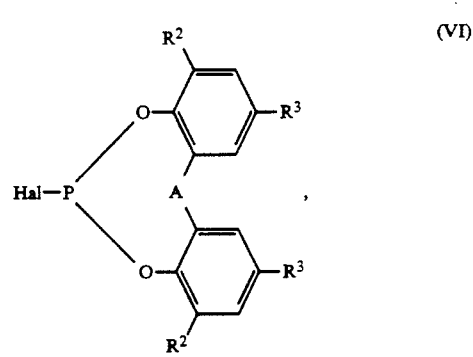

in which A, $R^2$, $R^3$ and Hal have the above-mentioned meaning, with the formation of the aryl phosphonites (V).

2. The process as claimed in claim 1, wherein Hal in the substituents of $R^1$ is chlorine or bromine.

3. The process as claimed in claim 2, wherein $R^1$ is naphthyl or a derivative thereof containing an alkyl radical of 1 to 4 carbon atoms.

4. The process as claimed in claim 1, wherein $R^2$ is a non-aromatic hydrocarbon radical having up to 12 carbon atoms.

5. The process as claimed in claim 4, wherein the non-aromatic hydrocarbon radical has 4 to 10 carbon atoms.

6. The process as claimed in claim 1, wherein the reaction temperature in the second step is between −30° C. and +30° C.

7. The process as claimed in claim 1, wherein the reaction temperature in the second steps is between −20° C. and +20° C.

8. An aryl phosphonite of the formula (I)

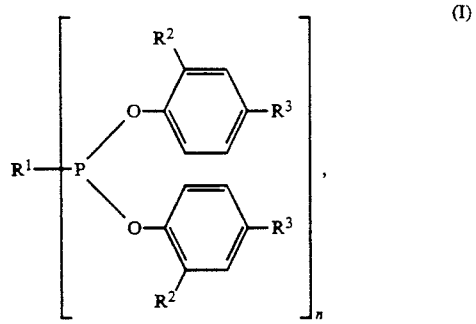

in which n is 1 or 2, $R^1$ as monovalent radical is a naphthyl radical which is unsubstituted or is substituted by 1 to 5 substituents, which can be identical or different and are a non-aromatic hydrocarbon radical, an alkoxy radical, an alkylthio radical or a dialkylamino radical, in which the alkyl radicals each have 1 to 8 carbon atoms, aryl or aryloxy each having 6 to 10 carbon atoms or halogen having an atomic number from 9 to 35, and as divalent radical a naphthylene radical which is unsubstituted or carries 1 to 4 non-aromatic hydrocarbon radicals each having 1 to 8 carbon atoms as substituents or a phenylene radical which is unsubstituted or is substituted by up to 2 non-aromatic hydrocarbon radicals each having 1 to 8 carbon atoms, $R^2$ is a non-aromatic hydrocarbon radical having 1 to 18 carbon atoms, aryl, arylmethyl, arylethyl or arylisopropyl, in which the aryl in each case contains 6 to 10 carbon atoms, and $R^3$ is hydrogen or a group mentioned under $R^2$.

9. The compound as claimed in claim 8, wherein n is 1, and $R^1$ is an unsubstituted or substituted naphthyl radical.

10. The compound as claimed in claim 9, wherein $R^2$ and $R^3$ each are alkyl radicals having 4 to 10 carbon atoms.

11. A process for the preparation of aryl phosphonites of the formula (I)

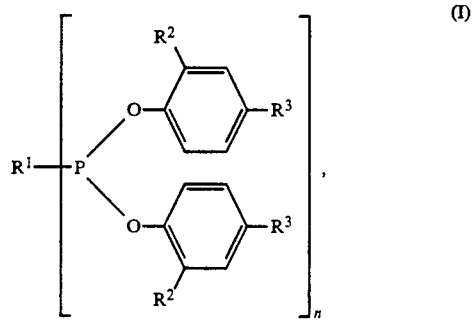

in which n and $R^1$, $R^2$ and $R^3$ have the meaning according to following claim 8, which comprises reacting in a first step a hydrocarbon halide $R^1(-Hal)_n$, in which $R^1$ has the above-mentioned meaning, n is=1 or 2 and the Hal is chlorine or bromine, under Grignard conditions with at least molar amounts of magnesium to give the corresponding Grignard compounds $R^1(MgHal)_n$ and reacting these in a second step at temperatures of from $-30°$ C. to $+30°$ C. with bisaryl halophosphonites of the formula (VI)

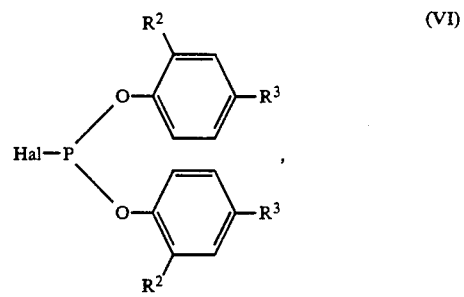

in which $R^2$, $R^3$ and Hal have the above-mentioned meaning, with the formation of the aryl phosphonites (I).

12. The process as claimed in claim 11, wherein the temperature of the second step is from $-20°$ C. to $+30°$ C.

13. A plastic molding composition containing a thermoplastic or thermoset plastic and an aryl phosphonite of the formula (I)

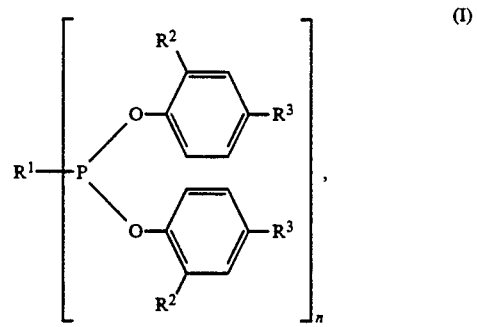

in a ratio of (90 to 99.99):(0.1 to 10), in which in formula (I) n, $R^1$, $R^2$ and $R^3$ have the same meaning as in claim 8.

14. The plastic molding composition as claimed in claim 13, wherein the plastic is a polyolefin.

15. The plastic molding composition as claimed in claim 14, wherein the polyolefin is polypropylene.

16. The plastic molding composition as claimed in claim 13, which contains
a) the thermoplastic or thermoset plastic,
b) the phosphonite of the formula (I) and
c) an ester of $c_1$) of 3,3-bis(3'-t-butyl-4'-hydroxyphenyl)butyric acid of the formula (III)

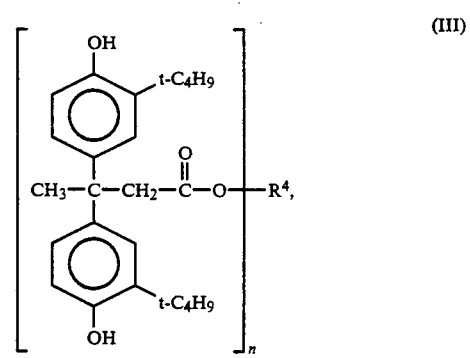

in which n is 1 or 2 and $R^4$ is a $C_1$- to $C_{12}$-alkyl radical, if n is 1, or is a $C_1$- to $C_{12}$-alkylene radical, if n is 2, or $c_2$) of β-(3,5-t-butyl-4-hydroxyphenyl)-propionic acid of the formula (IV)

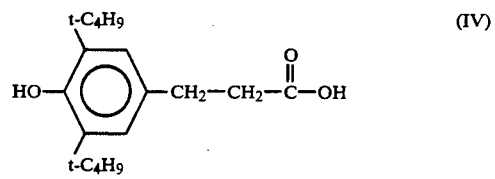

with a mono- to tetrahydric alcohol in a ratio of a:b:c of (90 to 99.98):(0.01 to 5):(0.01 to 5) % by weight.

17. A plastic molding composition as claimed in claim 13, which additionally contains additives from at least one member of the group consisting of antioxidants, UV absorbers, light stabilizers, metal deactivators, peroxide-destroying compounds, basic co-stabilizers, nucleating agents, fillers, reinforcing agents, plasticizers, lubricants, emulsifiers, pigments, optical brighteners, flame retardants, antistats or blowing agents.

* * * * *